(12) United States Patent
Wilkinson et al.

(10) Patent No.: US 8,806,951 B2
(45) Date of Patent: Aug. 19, 2014

(54) INSTRUMENT FOR DETERMINING A QUANTITY ASSOCIATED WITH A FORCE EXERTED ON A ROTOR

(75) Inventors: John Wilkinson, Gloucester (GB); Tim Jackson, Ledbury (GB)

(73) Assignee: Malvern Instruments, Ltd., Malvern (GB)

( * ) Notice: Subject to any disclaimer, the term of this patent is extended or adjusted under 35 U.S.C. 154(b) by 286 days.

(21) Appl. No.: 12/997,508

(22) PCT Filed: Jun. 10, 2009

(86) PCT No.: PCT/GB2009/001450
§ 371 (c)(1),
(2), (4) Date: May 11, 2011

(87) PCT Pub. No.: WO2009/150418
PCT Pub. Date: Dec. 17, 2009

(65) Prior Publication Data
US 2011/0203384 A1      Aug. 25, 2011

(30) Foreign Application Priority Data

Jun. 10, 2008   (GB) .................................. 0810570.2

(51) Int. Cl.
*G01N 3/00*        (2006.01)
(52) U.S. Cl.
USPC ....................... 73/788; 73/862.322
(58) Field of Classification Search
USPC ...................... 73/66, 788, 862.322
See application file for complete search history.

(56) References Cited

U.S. PATENT DOCUMENTS

| 4,037,886 A | * | 7/1977 | Boden et al. ................. 310/90.5 |
| 4,501,155 A | | 2/1985 | Garritano |

(Continued)

FOREIGN PATENT DOCUMENTS

| DE | 19708323 | 9/1997 |
| DE | 19632589 | 2/1998 |
| DE | 10209350 | 11/2003 |
| GB | 2289947 | 12/1995 |

OTHER PUBLICATIONS

Korea-Australia Rheology Jounral vol. 15 No. 4, Dec. 2003 pp. 187-196.

*Primary Examiner* — Max Noori
(74) *Attorney, Agent, or Firm* — Kristofer E. Elbing

(57) ABSTRACT

Rheometer, also usable for stress-strain-investigations, with at least one bearing (28; 35) having an adjustable stiffness in a direction normal to the bearing surfaces (19, 20, 21, 22, 23, 24, 26, 27). The instrument further includes a system (31, 32, 33, 34; 36, 37) for controlling a parameter for adjusting the stiffness of the at least one bearing (28; 35); a system (10) for determining a value of a quantity associated with a second force exerted between the rotor (8, 5, 6,7) and the stator (2) and opposing the force associated with the quantity to be determined; and a data processing system for correcting the determined value of the quantity associated with the second force by a bias value, obtained using a mapping having as a parameter a variable representative of the parameter for adjusting the stiffness.

30 Claims, 8 Drawing Sheets

(56) References Cited

U.S. PATENT DOCUMENTS

| | | | |
|---|---|---|---|
| 4,850,719 A * | 7/1989 | Moseley et al. | 384/1 |
| 5,302,874 A * | 4/1994 | Pinkerton | 310/90.5 |
| 5,469,006 A * | 11/1995 | Pinkerton | 310/90.5 |
| 5,633,547 A * | 5/1997 | Coombs | 310/90.5 |
| 6,191,513 B1 * | 2/2001 | Chen et al. | 310/90 |
| 7,017,393 B2 | 3/2006 | Doe et al. | |
| 7,252,000 B2 * | 8/2007 | Care et al. | 73/462 |
| 2005/0199043 A1 | 9/2005 | Doe et al. | |

* cited by examiner

INSTRUMENT FOR DETERMINING A QUANTITY ASSOCIATED WITH A FORCE EXERTED ON A ROTOR

This application is a US national phase application under 35 USC §371, and claims priority to PCT patent application number PCT/GB2009/001450 having an International filing date of Jun. 10, 2009, which, in turn, claims priority to United Kingdom patent application number GB 0810570.2 having a filing date of Jun. 10, 2008, both of which are herewith incorporated by reference.

The invention relates to rheometers and rheometric methods.

The invention relates in one general aspect to an instrument for determining a quantity associated with a force exerted on a rotor, which instrument includes:
a rotor;
a stator;
at least one bearing for mounting the rotor to allow at least limited displacement relative to the stator, the bearing including opposing bearing surfaces, arranged to be kept generally fixed in position, in use, relative to the rotor and stator, respectively,
at least one bearing having an adjustable stiffness in a direction normal to the bearing surfaces;
a system for controlling a parameter for adjusting the stiffness of the at least one bearing; and
a system for determining a value of a quantity associated with a second force exerted between the rotor and the stator and opposing the force associated with the quantity to be determined.

The invention also relates to a method of determining a quantity associated with a force exerted on a rotor,
wherein the rotor is mounted by at least one bearing so as to allow at least limited displacement relative to a stator, the bearing including opposing bearing surfaces, held generally fixed in position relative to the rotor and stator, respectively
wherein at least one bearing has an adjustable stiffness in a direction normal to the bearing surfaces, the method including
determining a value of a quantity associated with a second force exerted between the rotor and the stator and opposing the force associated with the quantity to be determined.

The invention also relates to a method of producing an instrument for determining a quantity associated with a force exerted on a rotor, which instrument includes:
a rotor;
a stator;
at least one bearing for mounting the rotor to allow at least limited displacement relative to the stator, the bearing including opposing bearing surfaces, arranged to be kept generally fixed in position relative to the rotor and stator, respectively,
at least one bearing having an adjustable stiffness in a direction normal to the bearing surfaces; and
a system for determining a value of a quantity associated with a second force exerted between the rotor and the stator and opposing the force associated with the quantity to be determined.

The invention also relates to a computer programme.

U.S. Pat. No. 4,501,155 discloses a rotational rheometer for the evaluation of rheological characteristics of a test specimen. The test specimen is shown in the form of a disk of polymer secured to a fixed table and coupled to a platen carried by a tubular carrier having a flange secured to a central rotor of the rheometer. The rotor is suspended for rotation about a longitudinal axis within a stator by means of a very low friction bearing in the form of a linear air bearing. A motor is controlled to apply torque to a shaft and hence to the rotor. Shaft position transducers are located in a transducer section for providing information pertaining to the angular position of the shaft and the longitudinal position of the shaft along the longitudinal axis. A control includes a compensation system which is operated prior to any test being performed on a test specimen in order, in essence, to calibrate the air bearing so that proper compensation for frictional forces will be available for use during a test. In the compensation system, the motor is used in a servo-loop to drive the rotor to selected angular positions. At each of those positions, the compensation system assures that the torque applied to the rotor by the motor will oppose exactly the unwanted torque exerted on the rotor by the forces generated in the air bearing at that position.

A problem of the known instruments is that the pressure of the air supplied to the bearing and hence its stiffness must be set prior to, and maintained constant during, the evaluation of the test specimen. If the test specimen has a high viscosity, then the air pressure will be set to a high value to provide the required stiffness. Using the same value for measurements on the same or a different specimen with a lower viscosity may lead to unnecessarily inaccurate measurements, because a large measured value of the torque will be compensated by a large friction value, to arrive at a relatively low value of the torque as exerted on or by the specimen.

It is an object of the invention to provide an instrument, methods and computer programme of the types mentioned above in the opening paragraphs that allow for accurate measurement over a wide range of values.

This object is achieved by the instrument according to the invention, which is characterised in that the instrument further includes a data processing system for correcting the determined value of the quantity associated with the second force by a bias value, obtained using a mapping having as a parameter a variable representative of the parameter for adjusting the stiffness. A quantity associated with a force can correspond to the force itself or a quantity directly related to it, e.g. torque, moment, etc.

Due to the use of a mapping having as a parameter a variable representative of the parameter for adjusting the stiffness, the stiffness of the bearing can be adjusted without the need to halt the measurement to re-calibrate the instrument. It is therefore possible to choose a larger stiffness where large forces on the rotor are to be expected, thus avoiding damage to the instrument (the bearing principally). The bias value will generally be larger, but not necessarily in relative terms by reference to the measured values. Where small forces on the rotor are to be expected, the bearing can be made less stiff, generally leading to lower bias forces and/or unintended displacements of the rotor. In that case, small values of the quantity associated with the second force are compensated by a small bias value, to arrive at a value of the quantity to be determined as output of the instrument. In an air pressure bearing or magnetic bearing—common examples of bearings with adjustable stiffness—small components of the pressure force or magnetic force parallel to the bearing surfaces will occur and increase as the forces in the direction normal to the bearing surfaces are increased.

In an embodiment, the instrument is configured to execute at least one routine for automatically determining a desired value of the parameter for adjusting the stiffness of the at least one bearing.

An effect is to aid in avoiding that a user damages the bearing or another component, or obtains invalid results, through an incorrect setting of the stiffness. The user cannot run a measurement with an inappropriate stiffness value, for example too low a value leading to too much movement of the bearing surfaces. Conversely, the user need not set the stiffness to too high a value as a precaution, so that measurements are not corrupted due to too high levels of torque bias in the bearing(s).

In a variant, the routine determines the desired value on the basis of at least one of:
- a variable representative of displacement of the rotor relative to the stator;
- a variable regulating a device for exerting a set moment between the rotor and the stator;
- input received through an interface for selecting a standardised operating procedure; and
- a variable representative of an actual distance between the bearing surfaces.

A variable representative of displacement of the rotor relative to the stator, e.g. displacement normal or parallel to the bearing surfaces, is a guide to the expected bias forces that can occur and/or to the risk of damage to the bearing. For example, displacement normal to the bearing surfaces will be an indicator of impending damage as the bearing surfaces move closer rapidly. High speeds parallel to the bearing surfaces where a known moment is applied to the rotor are an indication of a low opposing moment. For example, in a rheometer this would correspond to the presence of a low-viscosity sample. In such a situation, the stiffness of the bearing can be reduced. If a high set moment is to be exerted, then the bearing should be made stiffer. Input received through an interface for selecting a standardised operating procedure determines the kind of measurement to be carried out. A variable representative of an actual distance between the bearing surfaces is a useful indicator of whether the bearing is at risk to damage.

An embodiment of the instrument includes a system for mounting a specimen to be investigated between the stator and the rotor, such that the quantity to be determined corresponds to a moment exerted by the specimen when undergoing strain.

This is a useful application of the principles on which the instrument is based, because samples of material with widely differing mechanical properties exist. Displacement of the rotor relative to the stator causes the specimen to undergo strain. Applying a pre-determined amount of strain leads to stress with a value to be determined by the instrument and dependent on the properties of the specimen material. Applying a controlled moment results in strain that can similarly be measured. To correlate the values accurately and thus characterise the specimen, it is necessary to ensure that the pre-set moment is indeed that experienced by the specimen.

A variant of this embodiment includes a system for measuring at least one aspect of displacement of the rotor relative to the stator.

An effect is to allow stress to be related to strain, because the latter can be quantified on the basis of the measured displacement.

A variant is configured to execute at least one routine for continuously adjusting a desired value of the parameter for adjusting the stiffness of the at least one bearing during a measurement conducted on the specimen undergoing strain.

An effect is to maintain accurate measurement across a wide range of elasticity/viscosity values of the specimen. This is particularly useful when studying phase transitions and/or reactions occurring within the specimen. An example would be a curing process.

In an embodiment of the instrument, the rotor is mounted to allow rotational movement within a co-ordinate system fixed to the stator.

An effect is to allow continuous measurement.

An embodiment of the instrument includes a system for determining a position of the rotor relative to the stator, wherein the data processing system for correcting the determined value of the quantity associated with the second force by a bias value is configured to obtain the bias value using a mapping having as a further parameter a variable representative of the position of the rotor relative to the stator.

An effect is to compensate for irregular bias forces due to irregularities at the bearing surfaces and/or non-linearities in the system used to keep the bearing surfaces separated.

In an embodiment of the instrument, the at least one bearing having an adjustable stiffness includes a pressurised fluid bearing, and
the system for controlling a parameter for adjusting the stiffness includes a system for adjusting the pressure of fluid supplied to the pressurised fluid bearing.

An effect is that the mapping remains appropriate to the condition of the bearing. This is in contrast to a magnetic bearing, in which components of e.g. the rotor can become magnetised during use. A further effect is that there is no "start-up moment"—that is the moment required to move the bearing—like there is in mechanical bearings. Instead, there is a, much lower, offset torque. Typically, a mechanical bearing in a rotational rheometer, for example, would have a start-up torque of the order of 20 □Nm, whereas a pressurised air bearing would have an offset torque of the order of 100 nNm.

According to another aspect, the method of determining a quantity associated with a force exerted on a rotor according to the invention is characterised by correcting the determined value of the quantity associated with the second force by a bias value, obtained using a mapping having as a parameter a variable representative of the parameter for adjusting the stiffness. The method provides comparable effects to those provided by the instrument according to the invention, in use.

In an embodiment of the method, a desired value of the parameter for adjusting the stiffness of the at least one bearing is automatically determined.

In a variant, the desired value is determined on the basis of at least one of:
- a variable representative of displacement of the rotor relative to the stator;
- a variable regulating a device for exerting a set moment between the rotor and the stator;
- input received through an interface for selecting a standardised operating procedure; and
- a variable representative of an actual distance between the bearing surfaces.

An embodiment of the method includes
mounting a specimen to be investigated between the stator and the rotor, and
displacing the rotor relative to the stator so as to cause the specimen to undergo strain,
wherein the quantity to be determined corresponds to the moment exerted by the specimen when undergoing strain.

An embodiment of the method includes measuring at least one aspect of displacement of the rotor relative to the stator.

An embodiment of the method includes continuously adjusting a desired value of the parameter for adjusting the stiffness of the at least one bearing during a measurement conducted on the specimen.

In an embodiment of the method, the rotor is mounted to allow rotational movement within a co-ordinate system fixed to the stator.

An embodiment of the method includes
determining a position of the rotor relative to the stator, and
obtaining the bias value using a mapping having as a further parameter a variable representative of the position of the rotor relative to the stator.

An embodiment of the method, wherein the at least one bearing having an adjustable stiffness includes a pressurised fluid bearing, includes adjusting the pressure of fluid supplied to the pressurised fluid bearing.

According to another aspect, the method of producing an instrument for determining a quantity associated with a force exerted on a rotor according to the invention is characterised by obtaining data representative of a mapping between a bias value of the quantity, tending to oppose a direction of displacement of the rotor relative to the stator, and at least a variable representative of a parameter at least partly determining the stiffness of the at least one bearing.

The mapping thus obtained enables the stiffness of the bearing to be adjusted during use of the instrument whilst maintaining accuracy.

In an embodiment, wherein the instrument further includes a system determining a position of the rotor relative to the stator, the method further includes obtaining a mapping between the bias value and a further parameter comprising a variable representative of the position of the rotor relative to the stator.

The mapping thus obtained is more accurate, since non-linearities and/or irregularities in the bearing characteristics can be compensated for.

According to another aspect of the invention, there is provided a computer programme including a set of instructions capable, when incorporated in a machine-readable medium, of causing a system having information processing capabilities to perform a method according to the invention.

Another aspect of the invention provides an instrument for determining a quantity associated with a force exerted on a rotor, the instrument comprising:
 a rotor;
 a stator;
 at least one bearing for mounting the rotor to allow at least limited displacement relative to the stator, the bearing including opposing bearing surfaces arranged to be kept generally fixed in position, in use, relative to the rotor and stator respectively;
 at least one bearing having an adjustable stiffness in a direction normal to the bearing surfaces;
 means for adjusting the stiffness of the at least one bearing; and
 a system for determining a value of a quantity associated with a second force exerted between the rotor and the stator and opposing the force associated with quantity to be determined, wherein the instrument is arranged to
(i) determine a first measure of the quantity associated with the force on the rotor when the stiffness of the bearing is adjusted to a value corresponding to an upper limit for that quantity;
(ii) adjust the stiffness of the bearing to a value corresponding to said first measure; and
(iii) determine a second measure of the quantity associated with the force on the rotor when the stiffness of the bearing is adjusted to the value corresponding to the first measure.

Since the instrument is arranged to make a first, or preliminary, measure of the quantity associated with the force on rotor when the stiffness of the bearing is adjusted to a value corresponding to an upper limit for that quantity, the instrument is protected from damage that may occur if the rotor undergoes high angular acceleration and/or rotation through a large angle. The first, or preliminary, measure will typically be inaccurate because the stiffness of the bearing will be typically too high, as explained in above in relation to the rheometer disclosed in U.S. Pat. No. 4,501,155. However the stiffness of the bearing is then adjusted to a value corresponding to the first, or preliminary measure, and a second, more accurate, measure of the quantity associated with the force on the rotor is determined. In the case where an instrument according to this aspect of the invention is a rheometer for example, a sample of unknown viscosity may be measured with reduced risk of damage to the instrument. If the sample happens to have relatively low viscosity, an initial measurement of viscosity is made with the bearing adjusted to high stiffness, thus protecting the instrument. A second, more accurate measure of viscosity is then made with the stiffness of the bearing reduced to a value corresponding to the first measure of viscosity, thus providing a more accurate measurement.

This principle may be extended so that the stiffness of the bearing is subsequently set to a value corresponding to the second measure of the quantity associated with force on the rotor, and a third measure of that quantity determined, the third measure then being more accurate than the second measure. Fourth and subsequent measures of the quantity associated with the force on the rotor may be determined similarly to provide successively more accurate measures. The instrument may be arranged to stop making measurements of the quantity associated with the force exerted on the rotor when consecutive measurements converge to a required or predetermined degree.

The means for adjusting the stiffness of the at least one bearing may conveniently be a system for controlling a parameter of which the stiffness is, at least in part, a function. For example if the at least one bearing is a pressurised air bearing, the stiffness of the bearing may be adjusted by adjusting the pressure of the air supply to the bearing. If the bearing is a magnetic bearing, stiffness may be controlled by adjusting the current passing through the electromagnet of the bearing.

The instrument may optionally include a data processing system for correcting the determined value of the quantity associated with the second force by a bias value, obtained using a mapping having as a parameter a variable representative of the parameter for adjusting the stiffness.

A further aspect of the invention provides a method of determining a quantity associated with a force exerted on a rotor, wherein the rotor is mounted by at least one bearing so as to allow at least limited displacement relative to the stator, the bearing including opposing bearing surfaces held generally fixed in position relative to the rotor and stator respectively, wherein the at least one bearing has an adjustable stiffness in a direction normal to the bearing surfaces, the method including determining a value of a quantity associated with a second force exerted between the rotor and the stator respectively and opposing the force associated with the quantity to be determined, wherein the method comprises the steps of:

(i) determining a first measure of the quantity associated with the force on the rotor when the stiffness of the bearing is adjusted to an upper limit for that quantity;
(ii) adjusting the stiffness of the bearing to a value corresponding to said first measure; and
(iii) determining a second measure of the quantity associated with the force on the rotor when the stiffness of the bearing is adjusted to the value corresponding to the first measure.

The method may further include the steps of
(iv) setting the stiffness of the bearing to a value corresponding to the second measure of the quantity associated with the force on the rotor; and
(v) determining a third measure of said quantity when the stiffness of the bearing is set to a value corresponding to said second measure.

The method may include making a series of measures of the quantity associated with the force on the rotor, each measure being determined when the stiffness of the bearing is adjusted to a value corresponding to an immediately preceding measure in said series (or to an average, weighted or otherwise, of earlier measures).

A final answer value for the measured quantity may be determined when evaluating iterations of the value of the converge enough, or after a predetermined number of iterations.

Optionally, the method may include the step of correcting a determined value of the quantity associated with the second force by a bias value obtained using a mapping having as a parameter a variable representative of the parameter for adjusting the stiffness.

The invention will be explained in further detail with reference to the accompanying drawings, in which.

Figure 1:
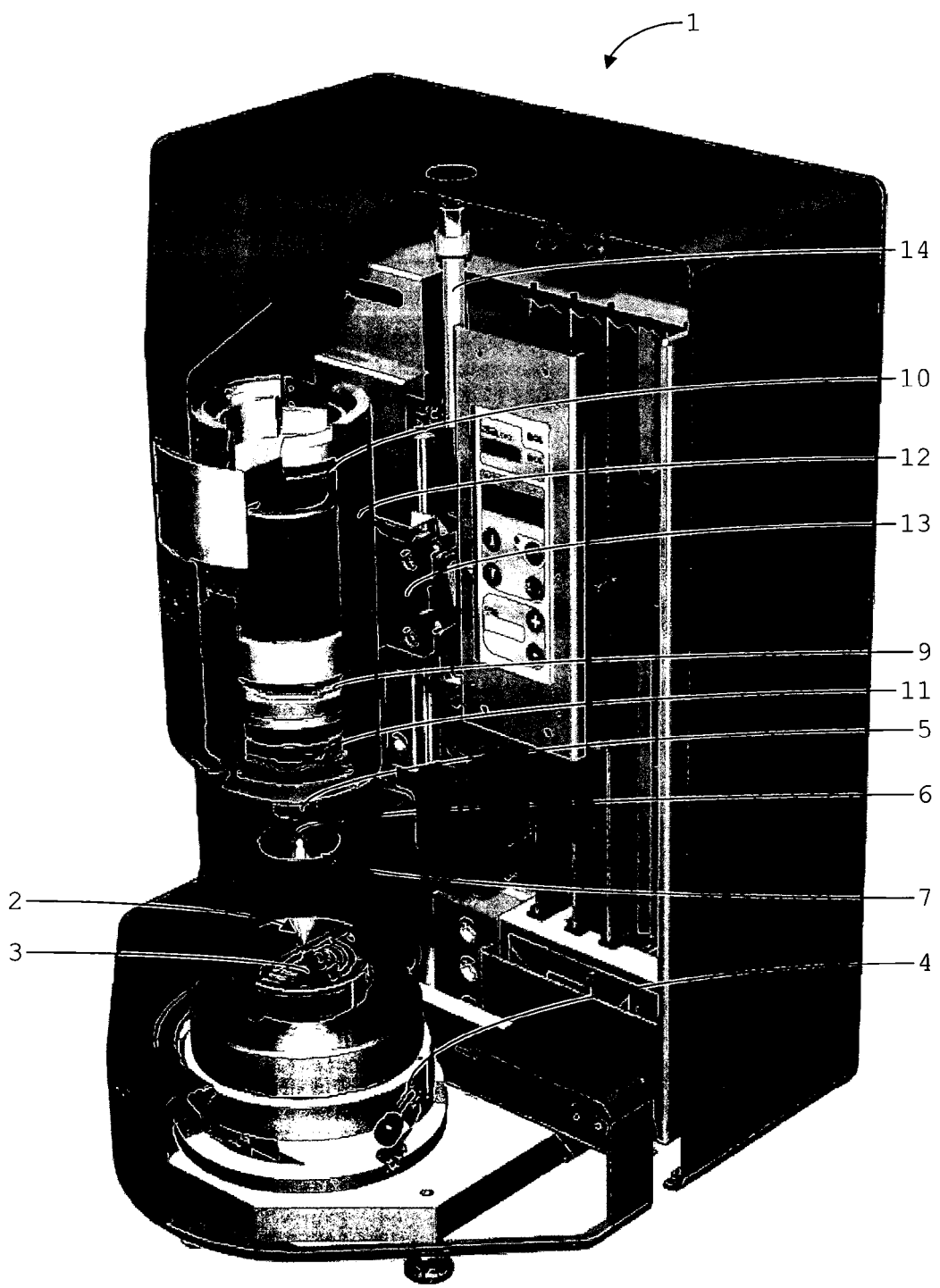
FIG. 1 is a schematic perspective view of several components of a rotational rheometer.

A typical rotational rheometer 1 includes a sample plate 2 for mounting a sample of material. In the illustrated embodiment, the sample plate is mounted above a temperature control unit 3. The sample plate 2 is fixed in position relative to a body of the rheometer 1. The sample plate 2 is merely representative of a variety of structures for mounting a sample. It can be replaced due to the presence of a clamping system 4 for holding the sample plate 2 and temperature control unit 3 in a fixed position relative to the body of the rheometer 1. Thus, for example, a cup (not shown) for holding a sample of material can be inserted in the clamping system 4. At least that component of the rheometer 1 that is held generally fixed in position relative to the body of the rheometer 1 will also be referred to herein as the "stator".

The rheometer 1 includes a chuck 5 for holding a probe 6. In the illustrated embodiment, the probe 6 includes a further sample plate 7 for contacting a specimen. In use, the specimen is sandwiched between the two sample plates 2,7. On one side, the specimen is entrained by the probe 6, whereas it is entrained by the sample plate 2 on the other side. Where there is a differential in movement, the specimen deforms. The rheometer 1 is used to relate the strain of the specimen to the stress exerted on it.

The combination of sample plates 2,7 is just an example of a workpiece geometry. Other types of workpiece can be used, depending primarily on the type of specimen to be analysed. Examples include a combination of a cup and a bob, a combination of a cone and a plate, etc. Each workpiece traps the specimen in a well-defined rheological condition.

Figure 2:
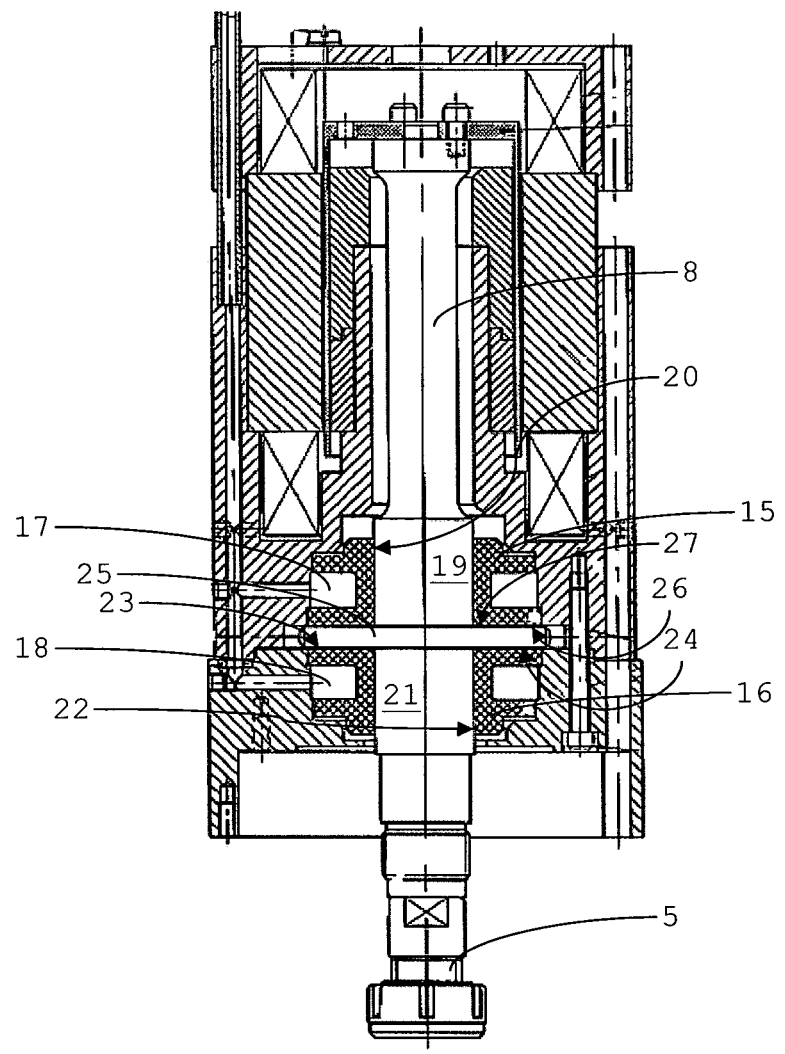
FIG. 2 is a cross-sectional view of a rotor of a rheometer mounted in an air bearing.

Referring also to FIG. 2, the chuck 5 is provided on a shaft 8 mounted by a bearing assembly 9, to be described in more detail below. A motor 10 is provided to actuate the shaft 8. In an embodiment, the motor 10 is an inductive motor having relatively low inertia and rapid transient response. The torque exerted by the motor 10 is controllable, and can be set relatively accurately, with temperature compensation. A position sensor assembly 11 allows for measurement of angular position and speed of the rotor relative to the body of the rheometer 1, and thus to the (stationary) sample plate 2. The position sensors comprised in the position sensor assembly are generally contactless, and allow for at least a differential position to be determined, which can be related to an absolute angular position. In an embodiment, the position sensor assembly 11 is further configured to measure at least one aspect (speed, distance) of displacement of the shaft 8, at least to a limited extent, in an axial direction thereof. As will be explained, the bearing assembly 9 allows such movement to a limited extent.

The components just described form a unit referred to herein as the bearing and motor assembly 12. The bearing and motor assembly 12 can be moved linearly relative to the body of the rheometer in a direction generally parallel to the longitudinal axis of the shaft 8. It is guided and supported by a linear bearing 13. In other embodiments there may be more than one linear bearing. The bearing and motor assembly 12 is positioned using a lead screw assembly 14. The lead screw assembly 14 includes a pre-tensioned nut and stepper motor (not shown in detail), and is provided to control at least one of the gap between the sample plates 2,7 and the normal force exerted on a specimen placed between the sample plates 2,7. It is noted that this force will be exerted also on part of the bearing assembly 9.

In the illustrated embodiment, the bearing assembly 9 comprises pressurised air bearings with adjustable stiffness. The stiffness refers to the change in separation between opposite bearing surfaces in response to a given force in a direction normal thereto. In a pressurised air bearing, the stiffness is adjusted by adjusting the pressure of the air supply to the bearing. In another embodiment, the bearing assembly 9 includes, or further includes, a magnetic bearing. In that case, the stiffness is adjusted by adjusting the current through an electromagnet comprised in the bearing.

Referring to FIG. 2, the bearing assembly 9 includes first and second bearing stators 15,16, in the shape of porous inserts. The bearing stators 15,16 can be made of porous carbon, for instance. First and second inlets 17,18 feed air to the stators 15,16. A first radial bearing surface 19 on the shaft 8 opposes an inner surface 20 of the first bearing stator 15. A second radial bearing surface 21 on the shaft 8 opposes an inner surface 22 of the second bearing stator 16. Thus, two radial bearings are provided. An upper bearing surface 23 of the second bearing stator 16 opposes a lower thrust bearing surface 24 of a thrust bearing component 25 integral to the shaft. A lower bearing surface 26 of the first bearing stator 15 opposes an upper thrust bearing surface 27 of the thrust bearing component 25.

In effect, the bearing assembly 9 comprises two radial bearings, allowing unlimited rotational movement of the shaft 8, and an axial bearing, allowing movement to a very limited extent in axial direction. In the illustrated embodiment, the air pressure between the upper bearing surface 23 and the lower thrust bearing surface 24 is the same as between the first radial bearing surface 19 and the inner surface 20, because there is a single inlet 17 for the first stator 15. In another embodiment, the stiffness of the or each radial bearing is controllable independently of the stiffness of the axial bearing. This can be achieved either by using separate supplies of pressurised air or by using an additional or alternative magnetic bearing for either the radial or the axial bearing, for example.

In practice, the bearing assembly 9, and in particular the bearing surfaces 19,20,21,22,23,24,26,27 are not perfectly rotationally symmetric, and the surfaces are not perfectly smooth. Due to such surface imperfections, rotational movement of the assembly of shaft 8, chuck 5 and probe 6 is opposed by an offset torque due to the pressurised air in the bearing assembly 9. Due to rotational asymmetries, the offset torque is dependent on the position of the shaft 8.

In each operational mode of the illustrated rheometer 1, the torque exerted between the shaft 8 and the motor 10 is determined. In another embodiment, the torque exerted on the sample plate 2 relative to the body of the rheometer is measured. The speed of the shaft 8 determines the shear rate of the specimen, and is also determined. Measurements can be taken in an oscillating mode, in which the amplitude and frequency of oscillation of the shaft 8 are determined. Measurements can also be taken at constant speed or at constant torque. In another mode of measurement, relaxation of the specimen after application of a particular strain is measured. The torque related to the stress of the specimen is not identical to that which is measured, on account of the torque offset discussed above. In yet another type of measurement, a very small set stress is applied and the strain response is measured (creep measurement), in order to determine the sample's visco-elastic response. In the illustrated instrument, the initially determined value of the torque is corrected with a bias value by a data processing system comprised in, or connected to, the rheometer 1. The bias value is obtained using a mapping of the torque offset value against both the position of the shaft 8 as determined by the position sensor assembly 11 and a parameter representative of the pressure of the air supplied to the bearing assembly 9.

The bearing mapping and application of the mapping may be by means of discrete maps at different air pressure values, interpolated maps across different air pressure values, extrapolated maps across different air pressure values or single value offsets (i.e. a single value for each of a plurality of different air pressure values).

Figure 3:
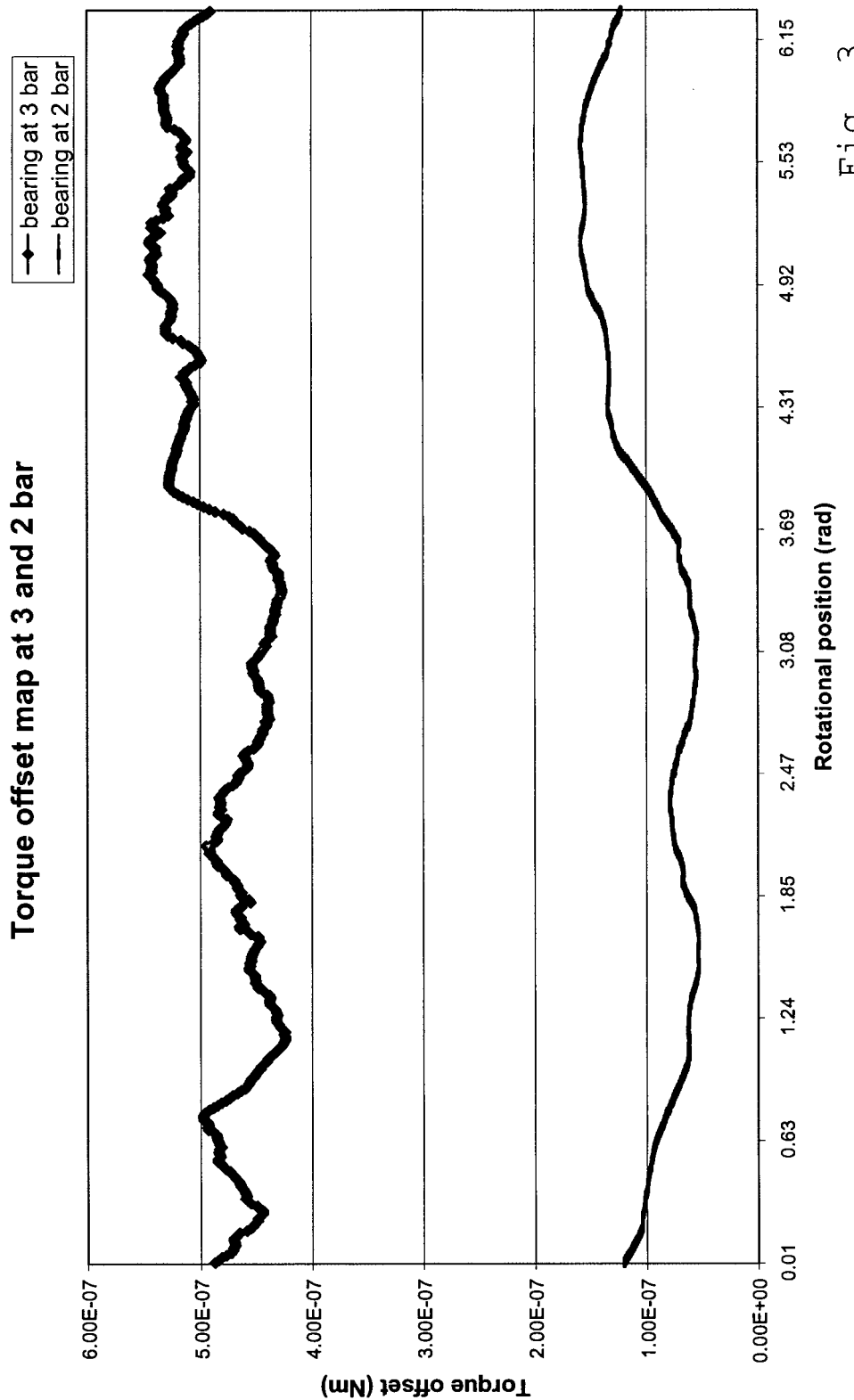
FIG. 3 is a diagram showing graphs of torque offset caused by a pressurised air bearing at different air supply pressures.

The magnitude of the offset torque in another example of a rotational rheometer with a pressurised air bearing assembly is shown in FIG. 3 at two different values of air pressure. Each graph plots the offset torque against angular position of the shaft 8. Each point along the x-axis corresponds to a particular angular position of the shaft at which a measurement was taken. One can see that each of the two graphs has an envelope (minimum to maximum value) indicative of the variation of offset torque with position. However, even the larger of the two envelopes is significantly smaller than the difference between the two graphs. This indicates that the air pressure has a larger effect on the offset torque. Since the envelopes of the two graphs are different, a mapping having as parameters both a variable representative of the parameter for adjusting the stiffness of the pressurised air bearings in the bearing assembly 9 and a variable representative of the position of the shaft 8 relative to the body of the rheometer 1 (and by implication the sample plate 2) allows for relatively accurate correction.

Modern rheometers are expected to be able to determine the flow and deformational parameters of samples ranging in type and properties from very low viscosity liquids such as water and solvents to very high modulus samples such as steel.

Sometimes this range of properties can be seen, and needs to be measured accurately, in one sample. An example is the measurement of the curing profile of a structural adhesive. Often these can start life as two fairly low viscosity components, which are mixed together and then optionally heated using the temperature control unit 3. Over time, the viscosity of the mixture decreases. If the activation energy for the cure is reached, the curing process starts and the components cure to a hard, sometimes brittle substance. This process can take anything from a few seconds (in the case of activated systems such as curing by Ultra-Violet light) to a few hours (samples that cure in ambient conditions). The change in modulus of the sample can be as much as ten or twelve orders of magnitude from start to finish.

Another scenario is the measurement of processing conditions. Rheometers are expected to be usable to model the processes that a sample experiences throughout its lifetime accurately. A typical example is constituted by emulsion paint. During manufacture, the particles that make up the paint are ground into small parts, which can then be emulsified. This is a high shear process. The emulsification process takes oil and water phases and uses surface active agents to create very small particles of oil (containing pigment)—this is the dispersed phase—suspended in water, the continuous phase. The size of the particle parts will affect the long-term stability of the product, for which reason the particles are ground using high shear. Once made, the paint will sit in the can for a long time, and be expected not to settle. The stresses exerted on the paint during storage are very low. The rheometer 1 is required to be able to characterise the propensity of a sample of such a composition to syneresis or flocculation. It also has to be able to reproduce high shears (such as occur during manufacturing or later stirring) as well.

Table 1 illustrates the requirements the rheometer 1 is configured to meet.

TABLE 1

| Measurement characteristics | Torque requirement | Speed requirement | Displacement measurement | Bearing |
|---|---|---|---|---|
| Accurate measurement of low viscosity samples | Low torques, e.g. in the range [1 μNm, 100 μNm] | Low speeds $\ll 1$ μrad/s | Accurate measurement of rotational displacement | Low torque offsets relative to measurement torque |
| Measuring samples with high modulus | High torques $>100$ mNm | Low-speed oscillation | Highly accurate measurement of rotational displacements $\sim 1$ nrad | Stiff bearing to reduce risk of damage |
| Measuring small stresses and speeds | Low torques, e.g. in the range [1 μNm, 100 μNm] | Low speeds $\ll 1$ μrad/s | Highly accurate measurement of rotational displacement | Low torque offsets relative to measurement torque |

TABLE 1-continued

| Measurement characteristics | Torque requirement | Speed requirement | Displacement measurement | Bearing |
|---|---|---|---|---|
| Measuring at very high speeds | Low to medium torque values in the range <50 mNm | Very high speed up to 600 rad/s | Accurate measurement of displacement at high speed | Stiff bearing to reduce risk of damage |

The rheometer 1 meets these conflicting requirements because it is configured to execute at least one routine for continuously adjusting a desired value the parameter for adjusting the stiffness of the at least one bearing in the bearing assembly 9 during a measurement conducted on the sample of material. Thus, for example, as a curing process develops, the bearing stiffness is adjusted. Concurrently, the mapping is used to obtain the correct torque offset value for correcting the measured torque.

The routine determines the desired value of the air pressure on the basis of at least one of:
a variable representative of displacement of the shaft 8 relative to the housing of the rheometer 1;
a variable regulating the motor 10 to exert a set moment on the shaft 8;
input received through an interface (e.g. provided by a computer connected to the rheometer 1 for selecting a standardised operating procedure; and
a variable representative of an actual distance between bearing surfaces, in particular the actual distance between the upper surface 23 of the second bearing stator 16 and the lower thrust bearing component surface 24.

The stiffness of the bearing can be increased when the bearing and motor assembly 12 is lowered along the linear bearing 13, using a routine to determine automatically the appropriate value of the air pressure on the basis of at least a variable representative of displacement of the shaft 8 relative to the housing of the rheometer 1. Alternatively or additionally, a routine based on selection of a standard operating procedure including the lowering of the bearing and motor assembly 12 can be used.

Input received through an interface (e.g. provided by a computer connected to the rheometer 1 for selecting a standardised operating procedure and/or a variable representative of an actual distance between bearing surfaces, in particular the actual distance between the upper surface 23 of the second bearing stator 16 and the lower thrust bearing component surface 24, can be used when measuring a sample exhibiting a relatively large non-zero first normal stress difference. Such a sample exerts a force in axial direction when strained through rotation. A stiffer bearing is required to avoid damage through contact between the upper surface 23 of the second bearing stator 16 and the lower thrust bearing component surface 24 or contact between the lower surface 26 of the first bearing stator 15 and the upper thrust bearing component surface 27. It is also required to allow this property of the sample to be measured accurately.

Summarising, the air pressure is set to a relatively low value for a low-torque measurement at low rotational speeds and for low axial force measurements at low changes in the gaps between the upper surface 23 of the second bearing stator 16 and the lower thrust bearing component surface 24 and between the lower surface 26 of the first bearing stator 15 and the upper thrust bearing component surface 27. The air pressure is automatically set to a relatively high value in the following modes of operation:
high-torque rotational measurements;
rotational measurements during which the product of speed and inertia is relatively high;
measurements where the gaps between the upper surface 23 of the second bearing stator 16 and the lower thrust bearing component surface 24 and between the lower surface 26 of the first bearing stator 15 and the upper thrust bearing component surface 27 change or are expected to change relatively rapidly in size;
measurements in situations where the axial force exerted on the probe 6 and thus the shaft 8 are, or are expected to be, relatively high;
placement or removal of a sample;
fitting or removal of the probe 6; and
an idle or power-off mode.

By dynamically changing the air pressure and applying the correct torque map data, the rheometer 1 can have a dynamic range of 1 nNm to 300 mNm. This dynamic range is available even to untrained users, since the instrument will automatically compensate for dynamic changes in the sample and use the most applicable pressure setting for measurement, giving the best data and protecting the instrument at the same time.

Figure 4:
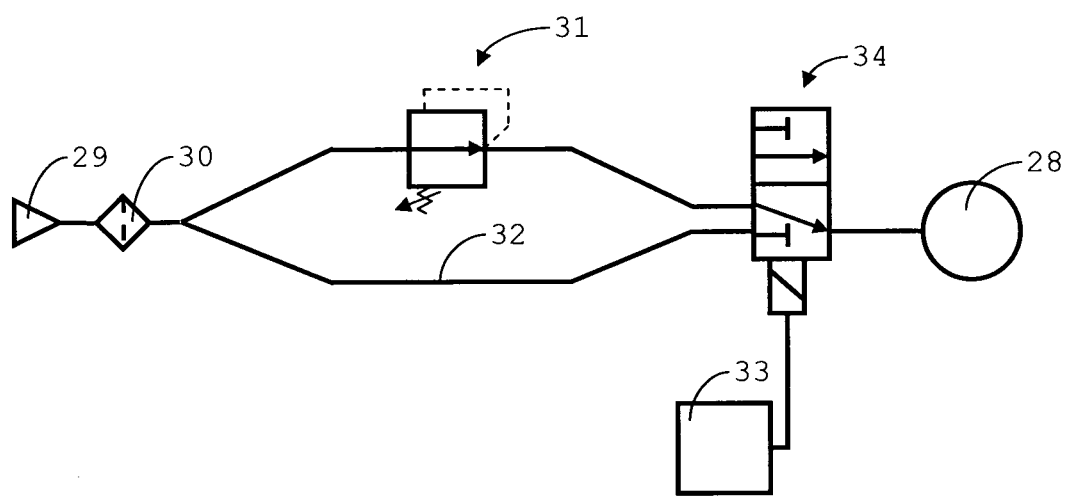
FIG. 4 is a schematic diagram of a first variant of a system including a pressurised air bearing with adjustable stiffness.

In a first variant, illustrated schematically in FIG. 4, the rheometer 1 comprises an air bearing 28 selectively supplied with air at one of two values of pressure. The system comprises means for connecting a source 29 and filter 30 to a precision regulator 31 set at a relatively low pressure and to a bypass conduit 32. A control unit 33 provides a selection signal to an air select valve 34 for selecting air from the precision regulator 31 or from the conduit bypassing the precision regulator 31. The mapping used to correct the measured torque values allows for switching without a noticeable jump in measurement data.

Figure 5:
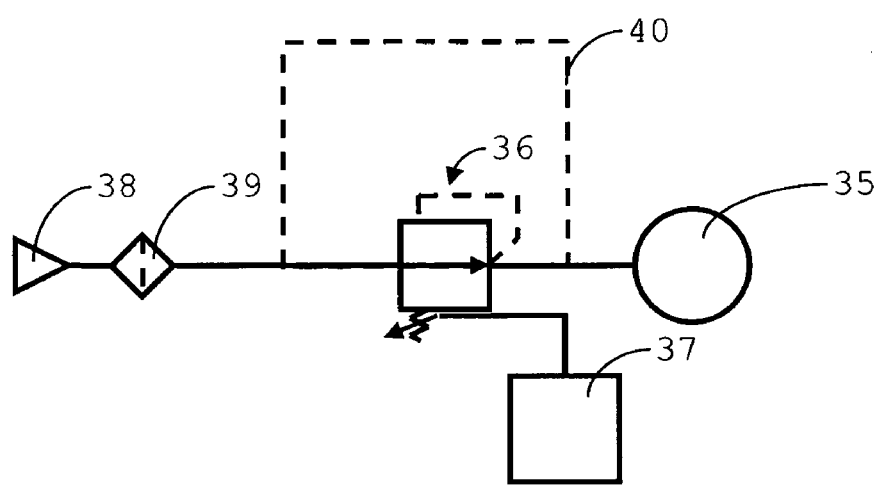
FIG. 5 is a schematic diagram of a second variant of a system including a pressurised air bearing with adjustable stiffness.

In a second variant, illustrated in FIG. 5, an air bearing 35 is supplied with air from a continuously variable pressure regulator 36. The continuously variable pressure regulator is controlled by a control unit 37, and supplied with air from a source 38 and filter 39. A bypass 40 is provided for increasing the stiffness of the air bearing 35 to a maximum value when the power supply to the instrument is off (the source 38 will generally be external to the rheometer, e.g. a laboratory air supply).

Figure 6:
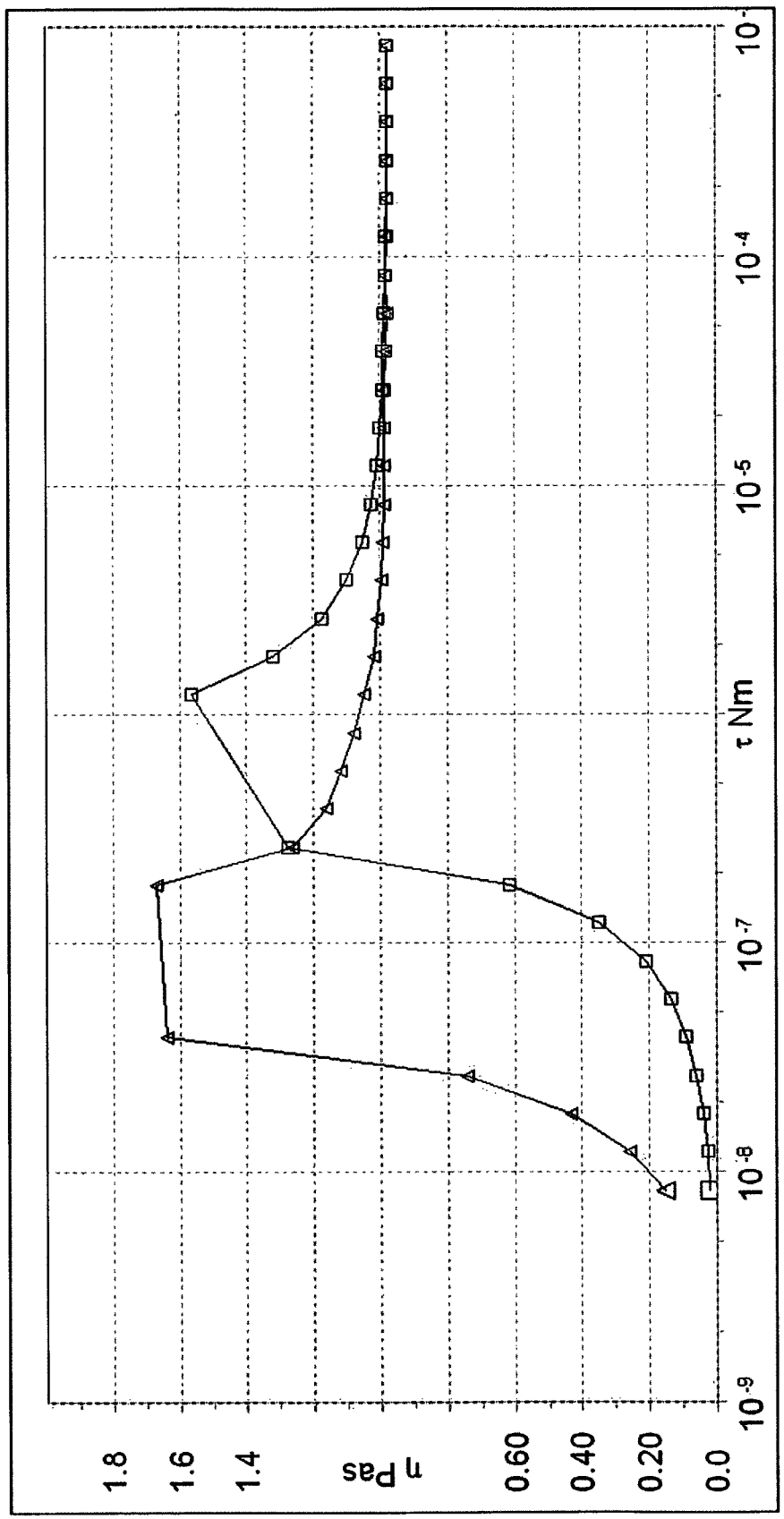
FIG. 6 is a first diagram showing the effect of applying a torque offset correction on viscometry data.
Figure 7:
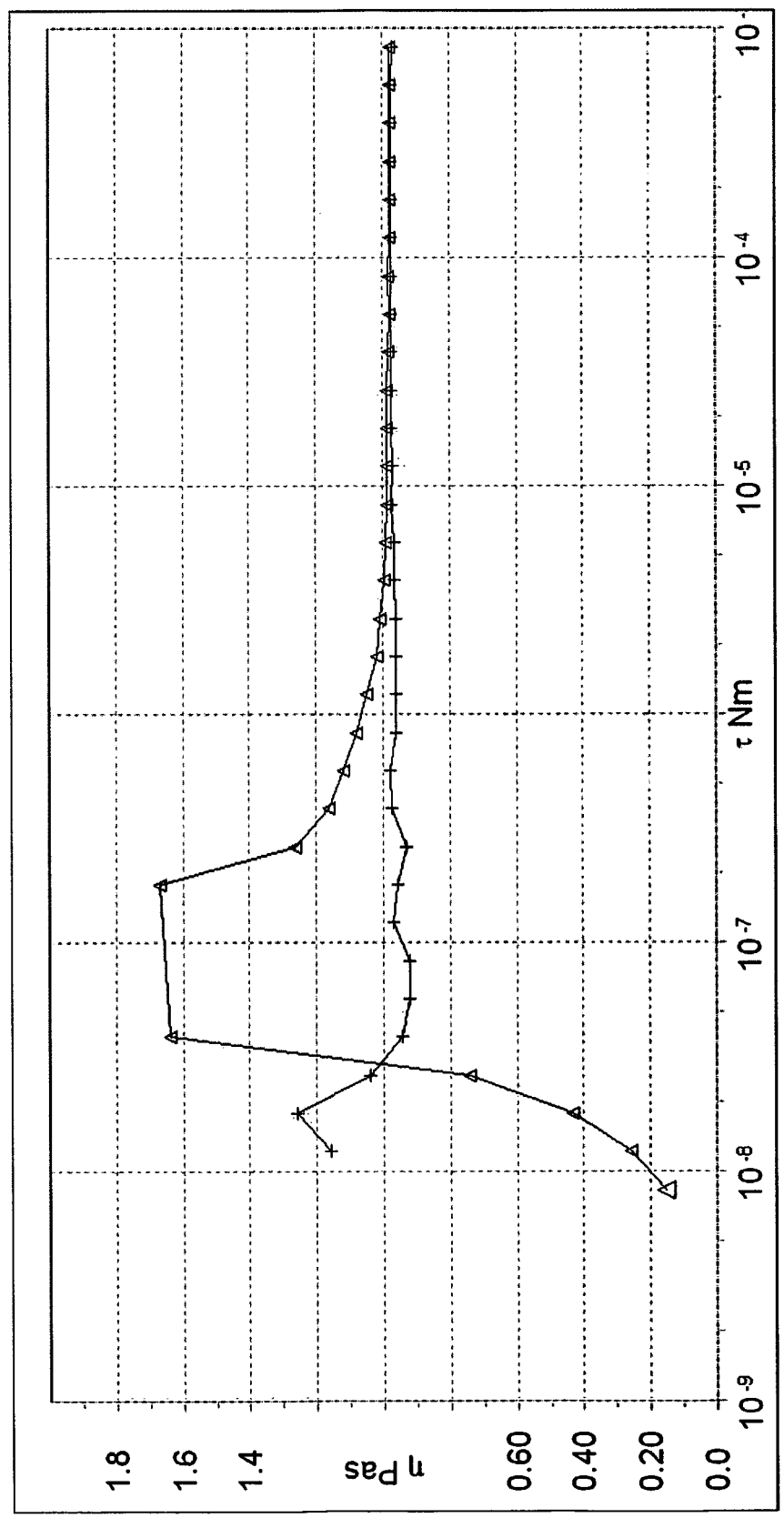
FIG. 7 is a second diagram showing the effect of applying a torque offset correction on viscometry data.
Figure 8:
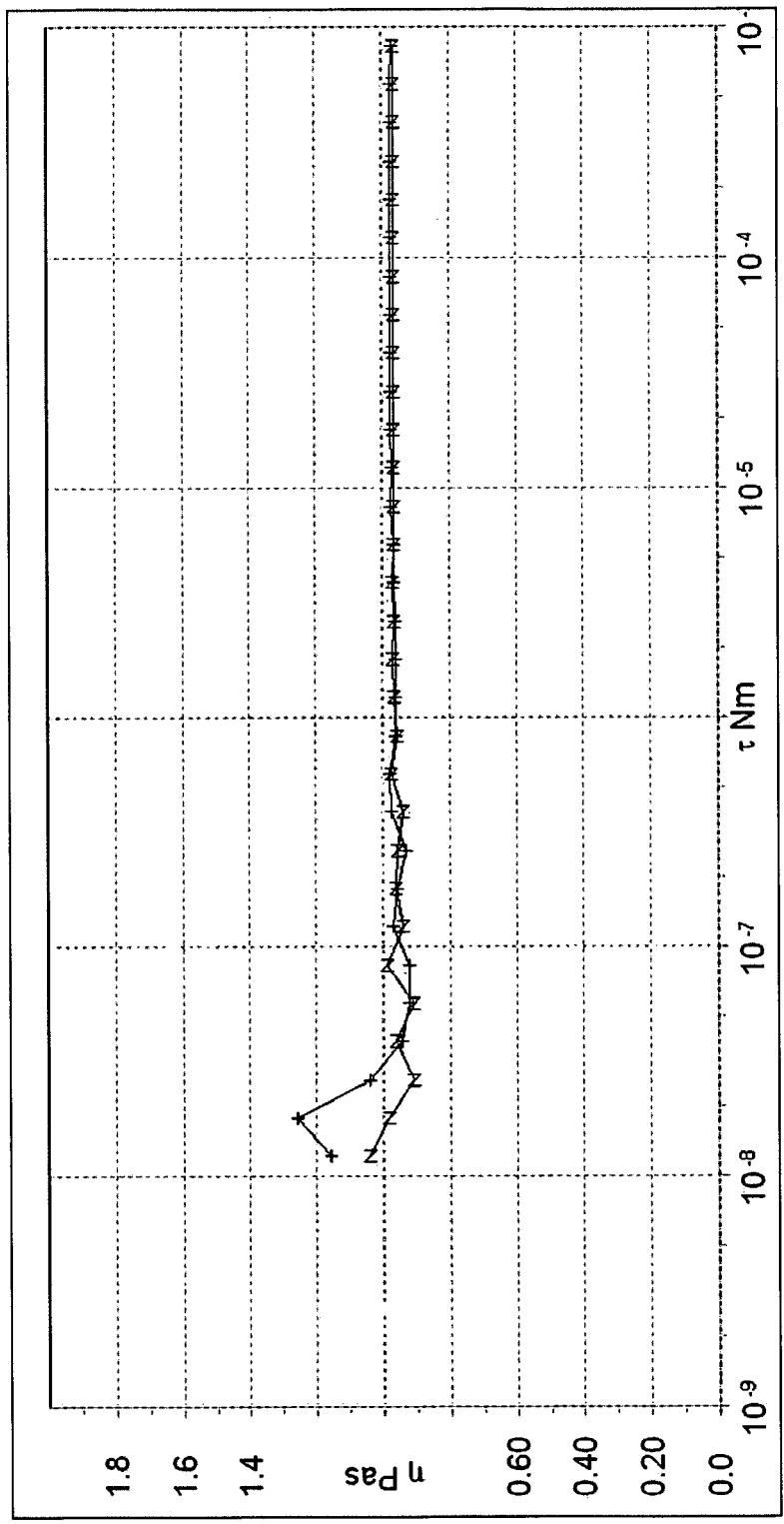
FIG. 8 is a diagram showing the effect of reducing the stiffness of the pressurised air bearing on the accuracy of measurement at low torque values.

FIGS. 6, 7 and 8 illustrate the effects of applying a mapping having as a parameter the air pressure of the bearing assembly 9 to viscometry data. Graphs in the diagrams of FIGS. 6 and 7 were obtained using a prototype instrument and air pressure at 3 bar. FIG. 8 shows the effect of reducing the air pressure. Both graphs in FIG. 8 were obtained using torque offset correction. The diagrams of FIGS. 6-8 illustrate that torque offset correction allows for accurate measurement of much lower torque values, because the deviations from the average viscosity value remain acceptably low down to lower torque values. FIG. 8 shows the benefit of reducing the air pressure supplied to the bearing assembly 9, in terms of the capability to measure lower torque values accurately.

The rheometer 1 described in detail above combines these properties in an instrument that automatically adjusts the stiffness of the bearings in the bearing assembly 9 to an appropriate value both to prevent damage to the bearings and to improve the accuracy of measurement.

A further example rheometer of the invention includes the structure indicated in FIGS. 1 and 2, and means arranged to make a series of torque measurements when a sample is placed on the stator 2. For the purposes of making the first measurement in the series, the stiffness of the pressurised air bearing is adjusted to correspond to a stiffness mapped to the highest value of torque in a range of torque values that might be expected, i.e. to an upper limit of stiffness. In other words a high bearing stiffness is implemented for the first measurement, for example by suitable control of the pressure of the air supply to the pressurised air bearing. The rheometer is thus afforded a degree of protection from damage that may occur in a case where a sample of relatively low viscosity is placed on the stator 2. In such a case a given torque applied by the probe 6, sample plate 7 and shaft 8 to the sample may cause an angular acceleration or angular deflection of the shaft 8 which is large enough to damage the rheometer in the absence of the stiff bearing. Although the first torque measurement may correspond to an inaccurate indication of viscosity, it is then used in a feedback arrangement to reduce the stiffness of the bearing towards a stiffness that is mapped to a value which corresponds to the first torque measurement. A second torque measurement is then made, and used in the feedback arrangement to further adjust the stiffness of the air-bearing. Subsequent torque measurements are made and used in a similar way.

The rheometer may if desired be arranged to make just two measurements of torque, with the second measurement being used to produce a final, accurate, value for viscosity. Alternatively the rheometer may be arranged to make a series of torque measurements corresponding to viscosity values of increasing accuracy. It may stop making measurements when consecutive torque measurements converge to a pre-determined extent. The final measurement in the series is then used to determine a viscosity value for the sample. The rheometer may establish a value for the viscosity of a sample within a fraction of a second, for example within a few milliseconds, or tens of milliseconds.

In this example there is a look-up table (or algorithm) correlating measured torque and the stiffness of the bearing to be used (or a parameter linked to bearing stiffness, such as air-pressure for an air-bearing, or electrical current for an electromagnetic bearing). The rheometer starts measuring the sample with a stiff bearing and uses information measured from the sample to reduce the stiffness of the bearing to a level suitable to the measured torque. There may be only two values of bearing stiffness employed, i.e. a high stiffness and a low stiffness, with the high stiffness being used when the measured torque is above a threshold value, for example $10^{-5}$ Nm. (However the threshold value may be greater than $10^{-5}$ Nm.) The rheometer can if required be arranged to employ a maximum bearing stiffness above the threshold value of measured torque, and for measured torque values below the threshold value, to employ one a plurality of discrete bearing stiffness values depending on the measured torque. Alternatively the bearing stiffness could be continuously varied according to measured torque below the threshold value. In addition, the peak or average measured torque may be monitored over a certain period of time, and the bearing stiffness adjusted to a value corresponding to that peak or average torque, in the manner described above, for a given period. The bearing stiffness may therefore be fixed within each of series of consecutive time periods; but may vary between those time periods.

This approach can help to reduce the chance of an unskilled operator of the rheometer accidentally damaging the rheometer by using a bearing that is too soft (i.e. having a stiffness that is too low) for a particular sample.

Of course if the viscosity of the sample changes over time the system may alter the bearing stiffness to suit the currently measured torque, or a predicted/selected value of torque. This "auto-start in safe mode" feature may in some embodiments be capable of being enabled/disabled by a user with appropriate authorisation codes.

The bearing assembly may include a magnetic bearing of adjustable stiffness, the stiffness of the bearing being controlled by the current passing through an electromagnet comprised in the bearing. Bearing stiffness may also be function of the axial position of the shaft 8, at least in part.

The invention is not limited to the embodiments described above, which can be varied with in the scope of the accompanying claims. Although the principles of the invention have been illustrated using the example of a rotational rheometer, they can equally be applied in a linear rheometer, where a rotor effects a linear movement relative to a stator with the sample placed in between. A moment determined by the force on the rotor and the distance between rotor and stator is opposed by frictional forces in the plane of the rotor and stator surfaces. The invention also finds application in other types of rotational instruments for determining a moment exerted on a rotor, e.g. in a galvanometer.

| LIST OF REFERENCE NUMERALS | |
|---|---|
| 1 | Rheometer |
| 2 | Sample plate |
| 3 | Temperature control unit |
| 4 | Clamping system |
| 5 | Chuck |
| 6 | Probe |
| 7 | $2^{nd}$ Sample plate |
| 8 | Shaft |
| 9 | Bearing assembly |
| 10 | Motor |
| 11 | Position sensor assembly |
| 12 | Bearing motor assembly |
| 13 | Linear bearing |
| 14 | Lead screw assembly |
| 15 | $1^{st}$ Bearing stator |
| 16 | $2^{nd}$ Bearing stator |
| 17 | $1^{st}$ Inlet |
| 18 | $2^{nd}$ Inlet |
| 19 | $1^{st}$ Radial bearing surface |
| 20 | Inner surface of $1^{st}$ bearing stator |
| 21 | $2^{nd}$ Radial bearing surface |
| 22 | Inner surface of $2^{nd}$ bearing stator |
| 23 | Upper surface of $2^{nd}$ bearing stator |
| 24 | Lower thrust bearing component surface |
| 25 | Thrust bearing component |
| 26 | Lower surface of $1^{st}$ bearing stator |
| 27 | Upper thrust bearing component surface |
| 28 | Air bearing |
| 29 | Source |
| 30 | Filter |
| 31 | Precision regulator |
| 32 | Bypass |
| 33 | Control unit |
| 34 | Air select valve |
| 35 | Air bearing |
| 36 | Variable pressure regulator |
| 37 | Control unit |
| 38 | Source |
| 39 | Filter |
| 40 | Bypass |

The invention claimed is:

1. Instrument for determining a quantity associated with a force exerted on a rotor, which instrument includes:
   a rotor;
   a stator;
   at least one bearing for mounting the rotor to allow at least limited displacement relative to the stator, the bearing including opposing bearing surfaces, arranged to be kept generally fixed in position, in use, relative to the rotor and stator, respectively, at least one bearing having an adjustable stiffness in a direction normal to the bearing surfaces;

a system for controlling a parameter for adjusting the stiffness of the at least one bearing; and a system for determining a value of a quantity associated with a second force exerted between the rotor and the stator and opposing the force associated with the quantity to be determined, wherein the instrument further includes a data processing system for correcting the determined value of the quantity associated with the second force by a bias value, obtained using a mapping having as a parameter a variable representative of the parameter for adjusting the stiffness.

2. Instrument according to claim 1, configured to execute at least one routine for automatically determining a desired value of the parameter for adjusting the stiffness of the at least one bearing.

3. Instrument according to claim 2, wherein the routine determines the desired value on the basis of at least one of:
a variable representative of displacement of the rotor relative to the stator;
a variable regulating a device for exerting a set moment between the rotor and the stator;
input received through an interface for selecting a standardised operating procedure; and
a variable representative of an actual distance between the bearing surfaces.

4. Instrument according to claim 3,
including a system for mounting a specimen to be investigated between the stator and the rotor, such that the quantity to be determined corresponds to a moment exerted by the specimen when undergoing strain,
including a system for measuring at least one aspect of displacement of the rotor relative to the stator,
configured to execute at least one routine for continuously adjusting (or adjusting repeatedly, from time to time) a desired value of the parameter for adjusting the stiffness of the at least one bearing during a measurement conducted on the specimen undergoing strain,
wherein the rotor is mounted to allow rotational movement within a co-ordinate system fixed to the stator,
including a system for determining a position of the rotor relative to the stator, wherein the data processing system for correcting the determined value of the quantity associated with the second force by a bias value is configured to obtain the bias value using a mapping having as a further parameter a variable representative of the position of the rotor relative to the stator,
wherein the at least one bearing having an adjustable stiffness includes a pressurised fluid bearing,
wherein the system for controlling a parameter for adjusting the stiffness includes a system for adjusting the pressure of fluid supplied to the pressurised fluid bearing,
further including a computer programme including a set of instructions capable, when incorporated in a machine-readable medium, of causing a system having information processing capabilities to (i) determine a first measure of the quantity associated with the force on the rotor when the stiffness of the bearing is adjusted to a value corresponding to an upper limit for that quantity, (ii) adjust the stiffness of the bearing to a value corresponding to said first measure, and
(iii) determine a second measure of the quantity associated with the force on the rotor when the stiffness of the bearing is adjusted to the value corresponding to the first measure, wherein the instrument is arranged to determine a series of measures of the quantity associated with the force on the rotor, each measure being determined when the stiffness of the bearing is adjusted to a value corresponding to an immediately preceding measure in said series, and wherein the instrument is arranged to stop determining measures of the quantity associated with the force on the rotor when measures in the series converge to a pre-determined degree.

5. Instrument according to claim 1, including
a system for mounting a specimen to be investigated between the stator and the rotor, such that the quantity to be determined corresponds to a moment exerted by the specimen when undergoing strain.

6. Instrument according to claim 5, including a system for measuring at least one aspect of displacement of the rotor relative to the stator.

7. Instrument according to claim 5, configured to execute at least one routine for continuously adjusting (or adjusting repeatedly, from time to time) a desired value of the parameter for adjusting the stiffness of the at least one bearing during a measurement conducted on the specimen undergoing strain.

8. Instrument according to claim 1, wherein the rotor is mounted to allow rotational movement within a co-ordinate system fixed to the stator.

9. Instrument according to claim 1, including
a system for determining a position of the rotor relative to the stator, wherein
the data processing system for correcting the determined value of the quantity associated with the second force by a bias value is configured to obtain the bias value using a mapping having as a further parameter a variable representative of the position of the rotor relative to the stator.

10. Instrument according to claim 1, wherein the at least one bearing having an adjustable stiffness includes a pressurised fluid bearing, and
wherein the system for controlling a parameter for adjusting the stiffness includes a system for adjusting the pressure of fluid supplied to the pressurised fluid bearing.

11. An instrument according to claim 1 wherein the instrument is arranged to
(i) determine a first measure of the quantity associated with the force on the rotor when the stiffness of the bearing is adjusted to a value corresponding to an upper limit for that quantity;
(ii) adjust the stiffness of the bearing to a value corresponding to said first measure; and
(iii) determine a second measure of the quantity associated with the force on the rotor when the stiffness of the bearing is adjusted to the value corresponding to the first measure.

12. An instrument according to claim 11 wherein the instrument is arranged to determine a series of measures of the quantity associated with the force on the rotor, each measure being determined when the stiffness of the bearing is adjusted to a value corresponding to an immediately preceding measure in said series.

13. An instrument according to claim 12 wherein the instrument is arranged to stop determining measures of the quantity associated with the force on the rotor when measures in the series converge to a pre-determined degree.

14. Method of determining a quantity associated with a force exerted on a rotor,
wherein the rotor is mounted by at least one bearing so as to allow at least limited displacement relative to a stator, the bearing including opposing bearing surfaces, held generally fixed in position relative to the rotor and stator, respectively wherein at least one bearing has an adjustable stiffness in a direction normal to the bearing surfaces, the method including determining a value of a quantity associated with a second force exerted between the rotor and the stator and opposing the force associated with the quantity to be determined, and correcting the determined value of the quantity associated with the second force by a bias value, obtained using a mapping having as a parameter a variable representative of the parameter for adjusting the stiffness.

15. An instrument according to claim 12 further including a computer programme including a set of instructions capable, when incorporated in a machine-readable medium, of causing a system having information processing capabilities to perform a method according to the steps recited in claim 14.

16. Method according to claim 15, wherein a desired value of the parameter for adjusting the stiffness of the at least one bearing is automatically determined.

17. Method according to claim 16, wherein the desired value is determined on the basis of at least one of:
- a variable representative of displacement of the rotor relative to the stator;
- a variable regulating a device for exerting a set moment between the rotor and the stator;
- input received through an interface for selecting a standardised operating procedure; and
- a variable representative of an actual distance between the bearing surfaces.

18. Method according to claim 17, including:
- mounting a specimen to be investigated between the stator and the rotor, and
- displacing the rotor relative to the stator so as to cause the specimen to undergo strain,
- wherein the quantity to be determined corresponds to the moment exerted by the specimen when undergoing strain,
- including measuring at least one aspect of displacement of the rotor relative to the stator,
- including continuously adjusting (or adjusting repeatedly, from time to time) a desired value of the parameter for adjusting the stiffness of the at least one bearing during a measurement conducted on the specimen,
- including:
  - determining a position of the rotor relative to the stator, and
  - obtaining the bias value using a mapping having as a further parameter a variable representative of the position of the rotor relative to the stator,
- wherein the at least one bearing having an adjustable stiffness includes a pressurised fluid bearing,
- including adjusting the pressure of fluid supplied to the pressurised fluid bearing,
- including the steps of:
  - (i) determining a first measure of the quantity associated with the force on the rotor when the stiffness of the bearing is adjusted to an upper limit for that quantity,
  - (ii) adjusting the stiffness of the bearing to a value corresponding to said first measure, and
  - (iii) determining a second measure of the quantity associated with the force on the rotor when the stiffness of the bearing is adjusted to the value corresponding to the first measure, and
- wherein a series of measures of the quantity associated with the force on the rotor are determined, each measure being determined when the stiffness of the bearing is adjusted to a value corresponding to an immediately preceding measure in said series.

19. Method according to claim 15, including
- mounting a specimen to be investigated between the stator and the rotor, and
- displacing the rotor relative to the stator so as to cause the specimen to undergo strain,
- wherein the quantity to be determined corresponds to the moment exerted by the specimen when undergoing strain.

20. Method according to claim 19, including measuring at least one aspect of displacement of the rotor relative to the stator.

21. Method according to claim 19, including continuously adjusting (or adjusting repeatedly, from time to time) a desired value of the parameter for adjusting the stiffness of the at least one bearing during a measurement conducted on the specimen.

22. Method according to claim 15, wherein the rotor is mounted to allow rotational movement within a co-ordinate system fixed to the stator.

23. Method according to claim 15, including
- determining a position of the rotor relative to the stator, and
- obtaining the bias value using a mapping having as a further parameter a variable representative of the position of the rotor relative to the stator.

24. Method according to claim 15, wherein the at least one bearing having an adjustable stiffness includes a pressurised fluid bearing, including
- adjusting the pressure of fluid supplied to the pressurised fluid bearing.

25. A method according to claim 15, the method including the steps of:
- (i) determining a first measure of the quantity associated with the force on the rotor when the stiffness of the bearing is adjusted to an upper limit for that quantity;
- (ii) adjusting the stiffness of the bearing to a value corresponding to said first measure; and
- (iii) determining a second measure of the quantity associated with the force on the rotor when the stiffness of the bearing is adjusted to the value corresponding to the first measure.

26. A method according to claim 25 wherein a series of measures of the quantity associated with the force on the rotor are determined, each measure being determined when the stiffness of the bearing is adjusted to a value corresponding to an immediately preceding measure in said series.

27. Computer programme including a set of instructions capable, when incorporated in a machine-readable medium, of causing a system having information processing capabilities to perform a method according to claim 15.

28. Method of producing an instrument for determining a quantity associated with a force exerted on a rotor, including:
- providing an instrument which includes:
  - a rotor;
  - a stator;
  - at least one bearing for mounting the rotor to allow at least limited displacement relative to the stator, the bearing including opposing bearing surfaces, arranged to be kept generally fixed in position relative to the rotor and stator, respectively, at least one bearing having an adjustable stiffness in a direction normal to the bearing surfaces; and a system for determining a value of a quantity associated with a second force exerted between the rotor and the stator and opposing the force associated with the quantity to be determined, and obtaining data representative of a mapping between a bias value of the quantity, tending to oppose a direction of displacement of the rotor relative to the stator, and at least a variable representative of a parameter at least partly determining the stiffness of the at least one bearing.

29. Method according to claim 28, wherein the instrument further includes a system determining a position of the rotor relative to the stator, further including obtaining a mapping between the bias value and a further parameter comprising a variable representative of the position of the rotor relative to the stator.

30. Computer programme including a set of instructions capable, when incorporated in a machine-readable medium, of causing a system having information processing capabilities to perform a method according to claim 28.

* * * * *